(12) United States Patent
Tuli et al.

(10) Patent No.: US 7,390,661 B2
(45) Date of Patent: *Jun. 24, 2008

(54) ARTIFICIAL BIDIRECTIONAL PROMOTER FOR ACTIVATION OF GENE EXPRESSION

(75) Inventors: Rakesh Tuli, New Delhi (IN); Sawant Samir Vishwanath, New Delhi (IN); Chandra Prakash Chaturvedi, New Delhi (IN); Kanti Kiran, New Delhi (IN); Rajesh Mehrotra, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 11/542,590

(22) Filed: Oct. 3, 2006

(65) Prior Publication Data

US 2007/0028323 A1  Feb. 1, 2007

Related U.S. Application Data

(62) Division of application No. 10/814,858, filed on Mar. 31, 2004, now Pat. No. 7,235,652.

(51) Int. Cl.
*C12N 5/14* (2006.01)
*C12N 5/04* (2006.01)
*C12N 15/00* (2006.01)
*C12N 15/09* (2006.01)
*C12N 15/11* (2006.01)
*C12P 21/06* (2006.01)
*A01H 1/00* (2006.01)

(52) U.S. Cl. .................. 435/410; 435/419; 435/320.1; 435/69.1; 800/278; 536/23.1; 536/24.1

(58) Field of Classification Search .................. None
See application file for complete search history.

(56) References Cited

U.S. PATENT DOCUMENTS 6,388,170 B1    5/2002    Gan et al.

OTHER PUBLICATIONS

Sawant, S. et al. "Designing of an Artificial Expression Cassette for the High-Level Expression of Transgenes in Plants" *Theor Appl Genet* (2001) vol. 102, pp. 635-644.
pUC19 map- downloaded Jul. 8, 2005.

*Primary Examiner*—Maria Marvich
(74) *Attorney, Agent, or Firm*—Ladas & Parry LLP

(57) ABSTRACT

A bidirectional module for activation of gene expression and regulation of transcription in both directions is disclosed. The bidirectional module comprises multiple cis regulatory DNA sequence elements, strategically arranged to give a 'Transcription Activating Module' that achieves high level expression from a 'Transcription Initiation Module'. The latter functions like a minimal promoter. The former activates transcription simultaneously in both the directions from the latter and also responds to several transcription inducing, external stimuli in both the directions. Since it is an artificially designed bidirectional transcription module, it has no equivalent DNA sequence in plant genome. This reduces the chances of the genes from being silenced by homology based mechanisms. A bidirectional promoter module as this, can therefore be used to develop efficient vectors for genetic engineering in plants.

3 Claims, 1 Drawing Sheet

Figure 1: Various constructs designed using the 'bidirectional DNA activation module' which were transformed in tobacco.

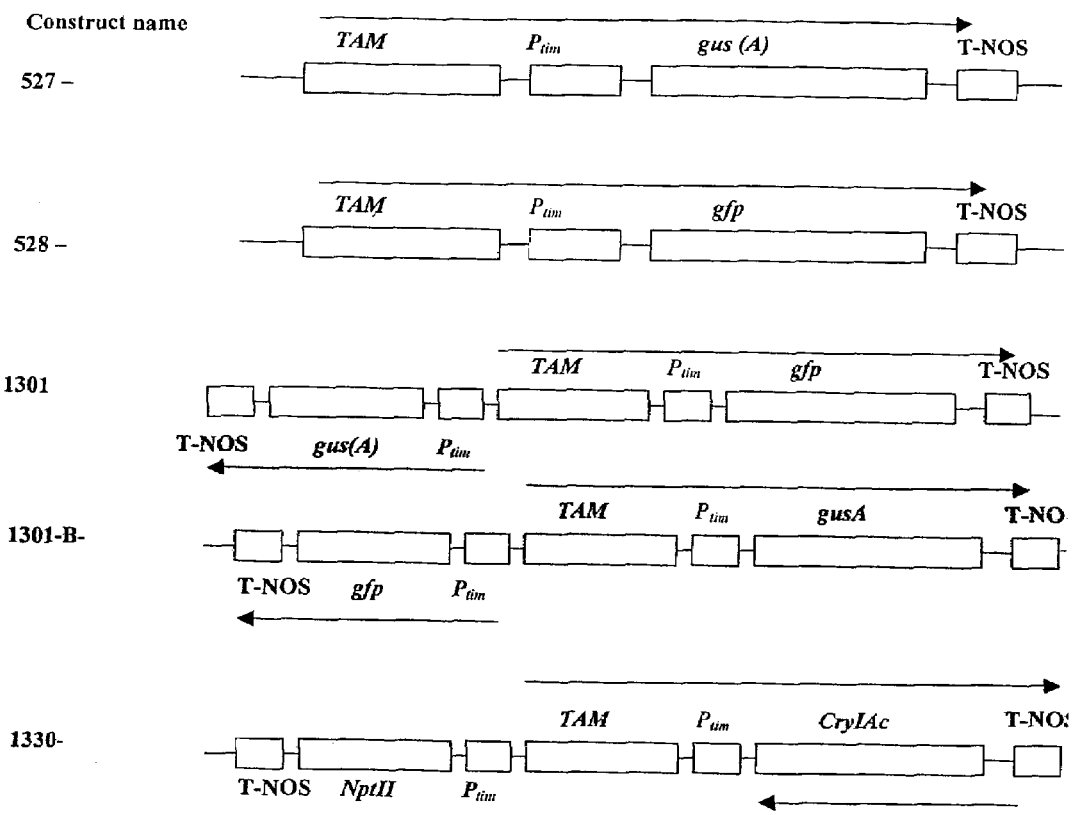

In above used figures:

| | | |
|---|---|---|
| TAM | = | Transcription Activation Module |
| $P_{tim}$ | = | Transcription Initiation Module |
| T-NOS | = | Nos-Poly Terminator |
| gusA | = | β-Glucuronidase Gene |
| gfp | = | Green Fluorescent Protein Gene |
| NptII | = | Neomycin Phosphotransferase Gene |
| CryIAc | = | δ-endotoxin crystal protein cry IAc |

ARTIFICIAL BIDIRECTIONAL PROMOTER FOR ACTIVATION OF GENE EXPRESSION

This application is a divisional, claiming the benefit thereof and incorporating by reference U.S. application Ser. No. 10/814,858, filed on Mar. 31, 2004, which issued on Jun. 6, 2007 as U.S. Pat. No. 7,235,652.

FIELD OF THE INVENTION

The present invention comprises the designing of a completely artificial bidirectional expression module that can also be referred to as bidirectional promoter module. The bidirectional module comprises multiple cis regulatory DNA sequence elements, strategically arranged to give a 'Transcription Activating Module' that achieves high level expression from a 'Transcription Initiation Module'. The latter functions like a minimal promoter. The former activates transcription simultaneously in both the directions from the latter and also responds to several transcription inducing, external stimuli in both the directions. Since it is an artificially designed bidirectional transcription module, it has no equivalent DNA sequence in plant genome. This reduces the chances of the genes from being silenced by homology based mechanisms. A bidirectional promoter module as this, can therefore be used to develop efficient vectors for genetic engineering in plants.

BACKGROUND OF THE INVENTION AND PRIOR ART

The process of gene expression involves two constitutive steps i.e., transcription and translation and leads to the formation of a protein or polypeptide or in some cases RNA with specific functions. The process of transcription is the most important regulatory step in the process of gene expression and its regulation. The initiation of transcription and modulation of gene expression in eukaryotic genes is directed by a variety of DNA sequence elements collectively arranged in a larger sequence called promoter. Promoter is the portion of DNA sequence on 5' side, i.e. before beginning of the coding region of a gene. It contains the signals for RNA polymerase machinery that initiates transcription and also modulates the level of transcription. Typical eukaryotic promoters consist of two parts—one, called the minimal or core promoter and the other, called upstream regulatory sequences or cis regulatory elements [Odell, J. T., Nagy, F, & Chua N.-H. *Nature* 313, 810-812 (1985) and Benfey, P. N. & Chua, N.-H. *Science* 250, 959-966 (1990)]

The minimal promoter or core promoter is a minimal stretch of contiguous DNA sequence that is sufficient to direct accurate initiation of transcription by RNA [Pol II machinery, Smale, S. T, *genes dev* 15, 2503-2508 (2001)]. A typical core promoter encompasses the site of initiation of transcription with several sequence motifs, which include TATA Box, initiator (Intr) sequence, TFIIB recognition elements (BRE) and other core promoter motifs [Jennifer, E. F. et al., *genes & dev* 16: 2583-2592 (2002)]. The core promoter provides the site of action to RNA polymerase II which is a multisubunit enzyme with the basal or general transcription factors like, TFIIA, B, D, E, F and H. These factors assemble into a transcription pre initiation complex (PIC) that catalyzes the synthesis of RNA from DNA template.

The activation of the core promoter is done by the additional sequence of regulatory DNA sequence elements to which various proteins bind and subsequently interact with the transcription initiation complex to activate gene expression. These regulatory elements comprise of DNA sequences that individually and/or in combination determine the spatiotemporal expression pattern of a promoter [Benfey, P.N., Ren, L. & Chua, N.-H *EMBO* 9: 1685-96 (1990)]. These short regulatory elements are located at a varying distance from transcription start point, some regulatory elements (called proximal elements) are adjacent to core promoter while other elements can be positioned several kilobases upstream or downstream of the promoter (enhancers). Both types of promoter elements modulate the level of transcription from core promoter [(Wasylyk B. CRC, *Critical Rev. Biochem,* 23: 77-120 (1988), Johnson & McKnight *Ann. Rev. Biochem.* 58: 799-839 (1989), Fussler & Gussin, *Method in Enzymology* 273: 3-29 (1996)]. Promoters are usually positioned 5' upstream relative to the transcription start site of coding region of the corresponding gene.

Transgenic plants are developed both, to improve desirable characters (like, yield, disease resistance, phytoremediation etc.) and to use them as protein factories. Often, there is need to introduce multiple genes to achieve the goals of genetic engineering. For example, almost always one gene is used (e.g., resistance to an antibiotics like kanamycin) to allow the selection of transgenic cells and tissues while a second gene is used (e.g., gene for enhancing yield or imparting resistance to a disease etc.) as the target gene to improve quality of the transgenic plant. Each such gene has to be normally expressed from its own promoter sequence. The most widely used constitutive promoters in the development of transgenic plants are the cauliflower mosaic virus 35S transcript promoter, and promoters of the nopaline and octapine synthase, ubiquitin promoter etc. However, introduction of multiple genes of interest into plants using repetitively the same promoter leads to gene silencing. In order to introduce multiple genes through genetic engineering, several strategies have been developed which include, sequential transformation using multiple gene constructs with different selectable markers, co-transformation with multiple constructs, genetic crosses between plants transformed with different constructs etc. One way to reduce the size of plant transformation vector and the number of promoters required while at the same time achieve the expression of multiple genes, will be to develop transcription regulatory signals that can initiate and regulate transcription in both the directions.

The use of bidirectional promoter can certainly overcome the limitation of sequential transformation and co-transformation with two genes. [Xie et al., *Nature Biotechnology,* 19: 677-679 (2001)] invented a method to convert a naturally occurring unidirectional or polar promoter into a bidirectional promoter. Such promoter can direct the expression of two genes or gene fusions at a time. Only a few types of strong promoters like CaMV 35S promoter have been reported and can be bidirectionalized. There is no earlier report of constructing a completely artificially designed promoter that would not have any long stretch of homology with native genomic DNA. It is very important to develop capability for designing artificial promoters with no sequence homology to genome since such promoters will not be silenced due to homology, [Davies et al., *The Plant Journal* 12, 791-804 (1997)].

The inventors of this work have earlier established [(U.S. patent application Ser. No. 09/263,692 now U.S. Pat. No. 6,639,065; EP 99301419.0-2106, Sawant et al., 2001, *Theor. Appl. Genet.* 102, 635-644)] the art of designing artificial synthetic promoters. Such prior synthetic promoter been described in detail in said references and are deemed to be incorporated herein by reference.:

The present invention is partly based on the finding that part of the artificial promoter shown in SEQ ID NO. 1 below:

```
                                                SEQ ID NO. 1
GTCGACCATCATTTGAAAGGGCCTCGGTAATACCATTGTGGAAAAAGTTG

GTAATACGGAAAAAGAAGATTCATCATCCAGAAAAGGTGTGGAAAAGTTG

TGGATTGCGTGGAAAAAGTTCGATCTGACCATCTCTAGATCGTGGAAAAA

GTTCACGTAAGCGCTTACGTACATATGTGGATTGTGGAAAAAGAAGACGG

AGGCATCGGTGGAAAAAGAAGCTTGTACGCTGTACGCTGACGATAGATAG

ATACACGTGCACGCGTCCACTTGACGCACAATTGACGCACAATGACGCCA

CTTGACGCTACT
``` can be used as an enhancer sequence or a 'Transcription Activating Module' (TAM). Another part of the sequence SEQ ID NO. 1, can be used as transcription initiator or a Transcription Initiator Module (TIM). The present invention teachers that the TAM activates and also regulates gene expression in both the directions from the TIM. Artificial synthesis of strong gene expression modules provides a tool to avoid the repetitive use of the so called strong promoters since a large variety of artificial promoters can be designed. Moreover, developing strong bidirectional promoter with multiple tissue specific or inducible characteristics will have major applications in the improvement of desired agronomical traits in plants. Designing of expression vectors for transformation using the so called bidirectional expression module will be of great value for transgenic development and biotechnology industries. The art of designing bidirectional promoters entirely by computational methods, as demonstrated here, provides a great deal of flexibility in genetic engineering.

Construction of synthetic gene expression modules is an important alternative to the dependence on natural promoters. This allows for bypassing gene silencing and also gives capability to regulate and improve expression level of valuable proteins or compounds of particular economic interest in plants. [(Rance, L et al., *Plant Science* 162: 833-842 (2002), combined three viral promoter sequences to generate highly active promoters that allowed strong transgene expression in plants)].

Authors of the present invention (Sawant S. et al., *Theor. Appl. Genet.* 102: 635-644) provided the only example for developing a completely artificial synthetic promoter designed for high level of expression in plants. The promoter (U.S. patent application Ser. No. 09/263,692, now U.S. Pat. No. 6,639,065 EP Application No. 99301419.0-2106) was developed by computational methods and demonstrated to express at a high level in a variety of plants and therefore, performed the purpose for which it was designed.

Prior to this invention, there are certain representative patents summarized below, which describe certain bidirectional promoters. U.S. Pat. No. 5,814,618 discloses a bidirectional promoter which has a multiple tet operator sequences. This patent shows that seven repeats of naturally found prokaryotic tet represser/operator/inducer sequences when flanked by two minimal promoters in the presence of tetracyclin inducer could direct the expression of two genes in eukaryotic cells. U.S. Pat. No. 595,564 discloses a bidirectional heterologous but again naturally existing construct for expression of transgenes in plants. U.S. Pat. No. 5,359,142 discloses natural promoter sequences, which have been manipulated to permit variation in enhancement of gene expression. U.S. Pat. No. 5,837,849 discloses yet another natural plant enhancer element that enhances the transcription level of a plant expressible gene. U.S. Pat. No. 5,627,046 discloses a naturally occurring bidirectional promoter. The art of making a eukaryotic polar promoter bidirectional is disclosed in U.S. Pat. No. 6,388,170. The inventors of that patent have used the art to bidirectionlize certain group of naturally occurring plant promoters such as CaMV 35S, PCISV, OPR, and SAG12.

OBJECTS OF THE INVENTION

It is an important object of the present invention to provide a method to computationally design and artificially synthesise a bidirectional transcription activation DNA module to modulate the level of expression of multiple transgenes in plants at the same time.

Another object of the present invention is to artificially design and chemically synthesise 'Transcription Initiation Module' to activate or initiate transcription and use it for expression from any 'Transcription Activation Module'.

It is yet another object of the present invention to provide a 'Transcription Initiation Module' that would decide the direction and point of initiation of transcription in a bidirectional promoter.

Another object of present invention is to make a totally artificially designed 'bidirectional expression module' by placing so called transcription initiation module on either or both sides of the so called 'Transcription activation module' for modulating expression of either or both genes in one or both directions.

Another object of the present invention is to provide computationally designed promoters which have no long stretch of homology with genomic DNA and therefore express the transgene stably in transgenic population and do not show silencing.

Another object of the present invention is to prove the functional validity of the sequence feature identified by the inventors for artificially designing and developing a novel 'bidirectional expression module', totally based on the nucleotide sequence analysis of database of genes selected for potential to express at high level in plants Yet another object of the present invention is to provide pant transformation vector using the so called 'bidirectional expression module' expressing selection marker gene like nptII (kanamycin resistance) or hptII (hygromycin resistance) or one useful gene in one direction and a reporter gene like GUS A, GFP or any other useful protein coding gene in other direction.

Yet another object of the present invention is to develop transgenic plants using the above designed plant transformation vectors and prove their utility in improving the desired agronomically important trait in plants.

SUMMARY OF THE INVENTION

The present invention is related to an advancement over the applicants' earlier invention cited above. More particularly, it relates to a novel artificially synthesized and strategically designed bidirectional gene expression module that can modulate the expression of one or two genes alone or together, in either or both the directions. This novel, bidirectional expression module has been selected as part of the total DNA sequence reported in the earlier invention that comprised of a chemically synthesized and theoretically designed DNA sequences. The present invention is based on the finding that part of the DNA sequence, called 'Transcription activation module' (TAM) shown as SEQ ID NO. 1 below:

```
                                                    SEQ ID NO. 1
GTCGACCATCATTTGAAAGGGCCTCGGTAATACCATTGTGGAAAAAGTTG

GTAATACGGAAAAAGAAGATTCATCATCCAGAAAAGGTGTGGAAAAGTTG

TGGATTGCGTGGAAAAAGTTCGATCTGACCATCTCTAGATCGTGGAAAAA

GTTCACGTAAGCGCTTACGTACATATGTGGATTGTGGAAAAAGAAGACGG

AGGCATCGGTGGAAAAAGAAGCTTGTACGCTGTACGCTGACGATAGATAG

ATACACGTGCACGCGTCCACTTGACGCACAATTGACGCACAATGACGCCA

CTTGACGCTACT
``` can activate transcription in either or both directions when a second component DNA sequence called 'transcription initiation module' (TIM) and shown as SEQ ID NO. 2

```
                                                    SEQ ID NO. 2
TCACTATATATAGGAAGTTCATTTCATTTGGAATGGACACGTGTTGTCAT

TTCTCAACAATTACCAACAACAACAAACAACAAACAACATTATACAATTAC

TATTTACAATTACATCTAGATAAACAATG
``` is placed in either or both the directions. Thus the first part i.e., 'Transcription Activation Module' (TAM) can modulate the expression of genes in both sense and antisense directions simultaneously, if a 'Transcription Initiation Module' (TIM) is placed strategically. The TIM is therefore, essential to utilize TAM. The former functions like a minimal or core promoter and is referred to in examples given here, as $P_{tim}$.

The 'Transcription Activation Module identified in the present invention is completely designed based on the nucleotide sequences in a database of genes selected for the potential to express at high level in plants. This activation module comprises of multiple cis-regulatory elements, which were identified in the upstream region 100 to 500 bp to the left or in 5' direction of transcription start site of highly expressible plant genes.

These cis-elements were computationally arranged to design an artificial 'Transcription Activation Module,' which can enhance the level of expression of genes in an orientation—independent manner in transgenic plants. Hence, the 'Transcription Activation Module' functions like a bidirectional transcription enhancing sequence.

Another feature of the present invention is identification from the earlier invention, a 'Transcription Initiation Module', which activates transcription of a gene placed downstream to the transcription start site. This so called 'Transcription Initiation Module' was designed based on characteristic features of nucleotide sequences in TATA box, transcription initiation site, untranslated leader and translational initiation regions in highly expressible plant genes in database.

The present invention, for the first time describes a totally artificially designed 'bidirectional expression module' comprised of 'transcription activation module' and 'transcription initiation module' based on the computational analysis of dataset of highly expressed plant genes from nucleic acid sequence database. Such an artificially designed sequence has no substantial equivalent or homologous sequence in plant. Hence, the artificially designed sequence is more stable in expression since it is not silenced due to homology based silencing of genes [(G. J Davies, M. A. Sheikh, O. J. Ratcliffe, G. Coupland and I. J. Furner, *The Plant Journal* 12, 791-804 (1997).] The results shown by this bidirectional expression module prove an additional and very useful function of the features earlier identified by the inventors. The invention demonstrates the potential of computational biology in designing and development of highly expressible bidirectional gene expression cassettes for tightly regulated, tissue specific, constitutive and inducible expression of multiple transgenes at a time in transgenic plants.

Another important aspect of the present invention is simultaneous enhancement in the expression of genes placed in both directions of the artificially designed synthetic 'transcription activation module' by a variety of cellular and environmental agents for example, the regulation of gene expression in response to salicylic acid, indole acetic acid, sodium chloride etc. in transgenic tobacco is demonstrated as part of the invention. This property of the bidirectional expression module shows that the transcription activation module of the present invention also functions like a chemically inducible bidirectional enhancer.

Thus the present invention provides a bidirectional promoter comprising:
  a) a Transcription Activation Module comprising of a chemically synthesised and strategically designed artificial nucleotide sequence having the sequence shown in SEQ ID NO. 1 or up to 70% homologous to it, and designed to enhance the level of expression of genes in plants;
  b) a Transcription Initiation Module comprising of a chemically synthesised and strategically designed artificial nucleotide sequence shown in SEQ ID NO. 2 or up to 70% homologous to it, and designed to function as a minimal sequence to initiate transcription of a gene placed downstream;

Preferably, said Transcription Initiation Module is located on either or both sides of the 'Transcription Activation Module' to express one or two genes, one at a time or both simultaneously for developing genetically engineered plants.

In another preferred embodiment, the Transcription Initiation Module is placed along 5' to 3' direction on either or both sides of Transcription Activation Module.

In an other preferred embodiment, the Transcription Initiation Module is placed along 5' to 3' direction on either or both sides of Transcription Activation Module.

Preferably, one or more genes of interest are placed downstream of the Transcription Activation Module for the purpose of their expression from one or both sides of the Transcription Activation Module.

In another preferred feature of the invention, said Transcription Activation Module comprises a DNA sequence having SEQ ID NO. 1 of signature sequences statistically identified as commonly present in highly expressed plant genes within −100-to −500 nucleotide positions upstream of the transcription initiation site in plants.

In another preferred feature of the invention, said Transcription Initiation Module comprises a DNA sequence having SEQ ID NO. 2 of signature sequences statistically identified as present within −100 nucleotides upstream of the transcription initiation site in natural promoters in plants.

The present invention also relates to Transgenic plants developed after stable transformation with the bidirectional promoter described above for the purpose of improving plant characteristics of interest to agriculture or industry.

The present invention also relates to a plant transformation vector comprising a bidirectional promoter as described above, expressing a selection marker such as nptII, bar, hpt etc. or any other such gene from one direction and a reporter gene such as gusA, gfp, luc or any other gene whose product can be conveniently monitored and the use of such vectors for development of transgenic plants.

In a preferred embodiment, the present invention relates to a bidirectional promoter comprising:

a) a Transcription Activation Module comprising of a chemically synthesised and strategically designed artificial nucleotide sequence having the sequence shown in SEQ ID NO. 1 or up to 70% homologous to it, and designed to enhance the level of expression of genes in plants;

b) a Transcription Initiation Module comprising of a chemically synthesised and strategically designed artificial nucleotide sequence shown in SEQ ID NO. 2 or up to 70% homologous to it, and designed to function as a minimal sequence to initiate transcription of a gene placed downstream;

c) said Transcription Initiation Module being located on either or both sides of the 'Transcription Activation Module' to express one or two genes, one at a time or both simultaneously for developing genetically engineered plants.

DETAILED DESCRIPTION OF INVENTION

The present invention will now be described in greater detail with reference to the accompanying drawings wherein:

FIG. 1 shows a number of gene constructs made in accordance with the present invention.

The present invention comprises artificial designing and chemical synthesis of a 'Bidirectional Transcription Activator DNA Module' which comprises of the multiple transcription cis-regulatory elements, which were identified in the upstream region (100-500) from the transcription start site of highly expressible plants genes. Detailed claims related to computational analysis based designing of highly expressing plant promoters have been filed earlier in the pending U.S. patent application Ser. No. 09/263,692 now U.S. Pat. No. 6,639,065 or EU. patent application Ser. No. 99301419.0-2106.

These so called cis-regulatory conserved sequence elements were strategically arranged on the bases of their percentage occurrence, there copy number and there most common position of occurrence in the dataset of highly expressed plant genes to from a completely novel Transcription Activation Module (SEQ ID NO. 1). The TAM is 312 bp long sequence whose critical function is activation or enhancement of transcription.

This so called synthetic 'Transcription Activation Module' of the present invention was used to design a completely novel artificially synthesised 'bidirectional expression module' that can enhance transcription in both sense and antisense directions when a 'Transcription Initiation Module' is placed in both the directions of the 'Transcription Activation Module'.

The so called 'Transcription Initiation Module' used in the present invention is also therotically designed and chemically synthesised, which was again designed based on the characteristic feature of nucleotide sequences of TATA-box proximal region in the set of highly expressed genes in plants (SEQ ID NO. 2). The TIM is 130 bp long and its critical function is to initiate the transcription of a gene when placed downstream of it.

The inventors have then utilized the so called 'Transcription Activation Module' and 'Transcription Initiation Module' to make a completely synthetic 'Bidirectional Expression Module', which modulates the expression of gene from both sense and antisense directions.

SEQ ID NO. 1 is 312 bp long and the SEQ ID NO. 2 is 130 bp long. A number of gene constructs used in the examples are shown in FIG. 1. The examples demonstrate the bidirectional function of the present invention. The invention for the first time describes a totally artificially designed 'bidirectional expression module' comprised of 'transcription activation module' and 'transcription initiation module' based on the computational analysis of dataset of highly expressed plant genes from nucleic acid sequence database. Such an artificially designed sequence has no substantial equivalent or homologous sequence in plant. Hence, the artificially designed sequence is more stable in expression since it is not silenced due to homology based silencing of genes [(G. J. Davies, M. A. Sheikh, O. J. Ratcliffe, G. Coupland and I. J. Furner, *The Plant Journal* 12, 791-804 (1997).] The results shown by this bidirectional expression module prove an additional and very useful function of the features earlier identified by the inventors. The invention demonstrates the potential of computational biology in designing and development of highly expressible bidirectional gene expression cassettes for tightly regulated, tissue specific, constitutive and inducible expression of multiple transgenes at a time in transgenic plants of the above two sequences. However, as is known to experts in this area, sequence variations to the extent of 30% may not affect function of the TAM and TIM. As also exemplified in an earlier patent application (U.S. Ser. No. 09/263,692 now U.S. Pat. No. 6,639,065 and EU 99301419.0-2106) several variations of the computationally designed sequence exist in nature.

The present invention will now be described with reference to the following non-limiting Examples, the purpose of which is to merely illustrate the invention.

EXAMPLE 1

Expression of a reporter gene (gusA) placed in sense orientation of 'Transcription Activation Module' (TAM) in transgenic tobacco plants.

TABLE 1

| Promoter with Gene construct (orientation) | Construct name and Plant designation | Glucuronidase activity (RFU/minute/mg protein) |
|---|---|---|
| Transgenic tobacco plants with TAM - $P_{tim}$ gusA (sense) | 527-1 | 324.2 |
| | 527-2 | 10.8 |
| | 527-5 | 197.5 |
| | 527-11 | 129.7 |
| | 527-16 | 257.0 |
| Control tobacco plant | — | 0 |

The gene for glucuronidase (gusA) was placed downstream of the artificially designed 'Transcription Initiation Module ($P_{tim}$) and such cassette was then placed to the right side (sense direction) of the artificially designed 'Transcription Activation Module (TAM) in 5' to 3' direction. In this case, no gene cassette was placed to the left side (antisense direction). The gene construct is shown in FIG. 1. It was made to demonstrate that the TAM activates transcription to the right even in absence of $P_{tim}$ or a gene on the left side. Transgenic tobacco plants were developed using *Agrobacterium tumefaciens* LBA 4404 containing kanamycin resistance gene as a selection marker (npt II) and the above construct TAM—Pmec gusA cloned in the well known and commercially available (Clontech, USA) binary vector pBI 101.

Results of gusA expression in five transgenic plants are given in Table 1. As seen, the TAM expresses the reporter gene gusA very efficiently in leaves of the transgenic tobacco plants. As expected, the activity varies from 10.8 in case of plant # 527-2 to 324.2 in case of # 527-1. Such variation in the level of expression is expected and is known to be due to the integration of transgene (gusA) at different positions on chromosomes of tobacco.

EXAMPLE 2

Expression of a second reporter gene (gfp) placed in sense orientation of 'Transcription Activation Module' in transgenic tobacco plants.

TABLE 2

| Promoter with Gene construct (orientation) | Plant designation | Green Fluorescence Protein activity (RFU/minute/mg protein) |
|---|---|---|
| Transgenic tobacco plants with TAM - $P_{tim}$ gfp (sense) | 528-12 | 881.0 |
| | 528-13 | 258.0 |
| | 528-15 | 203.0 |
| | 528-20 | 272.8 |
| | 528-32 | 165.5 |
| Control tobacco plant | — | 0 |

A reporter gene different from that taken in Example 1 was chosen in this case to show that the high level of expression from right of TAM was a general phenomenon and was not restricted to gusA. In this case, the gene for Green Fluorescence Protein (gfp) was placed downstream of the artificially designed transcription initiation module ($P_{tim}$) and such cassette was then placed to the right side (sense direction) of the artificially designed 'Transcription Activation Module' (TAM) in 5' to 3' direction. In this case, no gene cassette was placed to the left side (antisense direction) of TAM to demonstrate that TAM activates transcription to the right even in absence of a gene on the left side. Transgenic tobacco plants were developed using *Agrobacterium tumefaciens* LBA 4404 with a suitable selection marker (npt II) and the above construct TAM-$P_{tim}$ gfp in binary vector pBI 101. The gene construct is shown in FIG. 1. Results of gfp expression in five transgenic plants are given in Table 1. As seen, the TAM expresses the reporter gene gfp very efficiently in leaves of the transgenic tobacco plants. As expected, the activity varies from 165.5 in case of plant # 528.32 to 881.0 in case of # 528-12. Such variation in the level of expression is expected and is known to be due to the integration of transgene (gfp) at different positions on chromosomes of tobacco.

EXAMPLE 3

Expression of gusA and gfp placed in opposite orientations of the 'Transcription Activation Module' to demonstrate bidirectional function of the 'Transcription Activation Module' in transgenic tobacco plants.

TABLE 3

| Promoter with Gene construct (orientation) | Construct name and Plant designation | Glucuronidase activity (RFU/minute/mg protein) | Green Fluorescence Protein (RFU/minute/mg protein) |
|---|---|---|---|
| Transgenic tobacco plants with TAM - $P_{tim}$ gfp | 1301-1 | 92.8 | 560.0 |
| | 1301-2 | 165.5 | 412.7 |
| | 1301-3 | 170.7 | 862.2 |

TABLE 3-continued

| Promoter with Gene construct (orientation) | Construct name and Plant designation | Glucuronidase activity (RFU/minute/mg protein) | Green Fluorescence Protein (RFU/minute/mg protein) |
|---|---|---|---|
| (sense) + $P_{tim}$ - gusA (antisense) | 1301-4 | 75.3 | 340.0 |
| | 1301-5 | 229.7 | 257.0 |

In this example, expression of the two reporter genes described in the examples 1 and 2 was shown to be activated when these are placed on two opposite sides of the artificially designed bidirectional module TAM. Both the genes are expressed simultaneously in leaves of transgenic tobacco. The reporter gene gfp along with the artificially designed $P_{tim}$ was placed in the sense direction (right side of TAM) while gusA along with $P_{tim}$ was placed in antisense direction (left side of TAM). Both were in 5' to 3' direction along TAM. Transgenic tobacco plants were developed by using *Agrobacterium tumefaciens*, as in the earlier two examples and selected on the basis of kanamycin resistance. The results show that the two reporter genes expressed simultaneously in the two directions in all the plants. The level of expression of both the genes showed variation, as expected due to different positions of integration of transgene in the genome. The example establishes bidirectional nature of the module TAM viz., SEQ ID NO. 1 when it is used in format $P_{tim}$(antisense)-TAM-$P_{tim}$(sense) as shown in FIG. 1.

EXAMPLE 4

Simultaneous enhancement of the expression of genes placed in the two directions in response to induction of transcription by salicylic acid in transgenic tobacco plants.

TABLE 4

| | | % enhancement in activity 14 h after treatment of leaf with 100 µM salicylic acid | |
|---|---|---|---|
| Promoter with Gene construct (orientation) | Construct name and Plant designation | Glucuronidase | Green Fluorescence Protein |
| Transgenic tobacco plants with TAM- $P_{tim}$ gfp (sense) + $P_{tim}$ gusA (antisense) | 1301-1 | 160 | 171 |
| | 1301-2 | 370 | 240 |
| | 1301-3 | 5740 | 820 |
| | 1301-4 | 410 | 1927 |
| | 1301-5 | 78850 | 3110 |

This example illustrates that the artificially designed Transcription Activation Module (TAM) not only activates gene expression in both the directions, as shown in Example 3 but also shows further enhancement in expression in response to external stimuli as shown in Example 4. In this example, salicylic acid was used as an external stimulus. The results in Table 4 establish the TAM is capable of several fold enhancement by salicylic acid in both the directions simultaneously. For example, glucuronidase activity (gusA) was enhanced about 57 fold in transgenic plant # 1301-3. Simultaneously, in the same plant, Green Fluorescence Protein (gfp) was also enhanced 8 fold. The former was in antisense direction while the latter was in sense direction as also shown in the gene construct in FIG. 1. Similarly, in plant # 1301-5, about 788 fold increase was noticed for gusA (antisense direction) while 31 fold increase was noticed for gfp (sense direction). The results establish that TAM responded to salicylic acid in both the directions. However, the extent of enhancement could be different in the two directions.

EXAMPLE 5

Simultaneous enhancement of expression of genes placed in two directions in response to Induction of Transcription initiation by NaCl and IAA.

TABLE 5

| Promoter with Gene construct (orientation) | Construct name and Plant designation | % enhancement in activity, 14 h after treatment of leaf with 400 mM NaCl | |
|---|---|---|---|
| | | Glucu-ronidase | Green Fluorescence Protein |
| Transgenic tobacco plants with TAM-$P_{tim}$ gfp (Sense) + $P_{tim}$ gusA (Antisense) | 1301-1 | 298 | 755 |
| | 1301-2 | 169 | 769 |
| | 1301-3 | 971 | 1200 |
| | 1301-4 | 794 | 1071 |
| | 1301-5 | 348 | 1025 |

This example illustrates that the designed 'Bidirectional expression module' like in example 5a shows further increase as expression in response to NaCl (Sodium Chloride) treatment. The result in Table 5 shows that the TAM in transgenic line 1301-3 shows about 10 fold increase in (GUS activity) in antisense direction and 12 fold increase in GFP in sense direction. The different level of expression of gusA and GFP in different transgenic lines varies, which is due to position of integration of transgene in the genome. The gene construct is shown in FIG. 1. The transgenic plants were same as described in Table 4.

EXAMPLE 6

Enhancement of the expression of genes placed in two directions in response to induction of transcription by Indole Acetic Acid (IAA) in transgenic tobacco plants.

TABLE 6

| Promoter with Gene construct (orientation) | Construct name and Plant designation | % enhancement in activity 14 h after treatment of leaf with 50 µM IAA | |
|---|---|---|---|
| | | Glucu-ronidase | Green Fluorescence Protein |
| Transgenic tobacco plants with TAM-$P_{tim}$ gfp (Sense) + $P_{tim}$ gusA (Antisense) | 1301-1 | 378 | 301.06 |
| | 1301-2 | 521 | 500 |
| | 1301-3 | 517 | 608 |
| | 1301-4 | 672 | 2170 |
| | 1301-5 | 425 | 782 |

The example shows the increase in gusA and gfp activity on IAA (indole acetic acid) treatment to the transgenic tobacco leaves. The glucuronidase activity (gusA) was enhanced by about 7 fold in transgenic plant 1301-4. In the same plant, gfp were enhanced 22 fold. In plant 1301-5 (antisense direction) there was 4 fold increase in gus activity and 8 fold increase in gfp (sense direction). The results shown in the examples 4, 5 and 6 show the chemically inducible behavior of the synthetic 'Transcription Activation Module' modulating expression in both the directions.

EXAMPLE 7

Development of agronomically improved tobacco plants by expressing and insecticidal protein from bidirectional enhancer.

TABLE 7

| Promoter with Gene Construct (orientation) | Plant designation | % Mortality of larvae of Helicoverpa |
|---|---|---|
| Transgenic tobacco plant with TAM - $P_{tim}$ cryIAc (sense) $P_{tim}$ nptII (antisense) | 1330-1 | 100/100 |
| | 1330-2 | 100/100 |
| | 1330-3 | 90/100 |
| | 1330-4 | 89/100 |
| | 1330-5 | 95/100 |

This example establishes that the artificially designed transcription activation module can be used to develop a vector for transformation of plants and for the development of transgenic plants improved for better agricultural performance. In this example, a well known selection marker gene for kanamycin resistance (nptII) along with $P_{tim}$ was placed to the left (antisense strand) of TAM to allow the selection of transgenic plants on the basis of resistance to kanamycin. An agronomically highly valuable gene cryIAc—called as the crystal protein gene (originally cloned from a soil bacterium, *Bacillus thuringiensis*) was placed along with $P_{tim}$ on the right side (sense direction) of TAM. The cryIAc codes for a protein highly toxic to the larvae of lepidopteran insects *Helicoverpa* sp. etc. The transgenic plants were selected for resistance to kanamycin. All five selected transgenic plants showed the expression of the insecticidal protein CryIAc in range 0.07 to 0.16% of total soluble leaf protein as estimated by ELISA. All five plants were toxic to the larvae and gave 89 to 100% mortality of $1^{st}$ instar larvae fed on the leaves of transgenic tobacco plants. The results establish that the completely artificially designed sequence TAM in combination with $P_{tim}$ can be used to develop bidirectional promoter-based vectors which can be used for the development of transgenic plants of high value to industry. Similar results were obtained when transgenic cotton lines were developed. Insect toxic Coker cotton lines that expressed the δ-endotoxins from a similar bidirectional module were obtained. These were highly resistant to feeding damage by lepidopteran pests, including two major bollworms, called *Helicoverpa* sp. and *Spodoptera* sp.

CONCLUSION

To prove the validity and features of the designed 'Bidirectional Expression Module' the inventors made various gene constructs using reporter genes glucuronidase A (gusA or GUS), green fluorescence protein (gfp), δ-endotoxin (cry) etc. which were placed in both sense and antisense directions (FIG. 1) of the expression module and used in the Examples. The expression patterns of the reporter genes are similar and comparable in both sense and antisense directions, when taken one at a time (Examples 1 and 2) or two at a time (Examples 3, 4, 5, 6, 7) with expected extent of variation in the level of expression within different lines carrying the same construct. Such variation in the level of expression is expected and known to be due to the integration of transgenes at different positions on chromosomes of the target plant.

Another important feature which the inventors have shown is the chemically inducible behaviour of the designed 'Transcription Activation Module' which not only enhances gene expression in both directions as shown in examples (4, 5 and 6) but also shows further enhancement in the expression in response to salicylic acid treatment (Example 4) or other environmental milieus (Example 5). The results indicate several fold enhancement by salicylic acid in both directions simultaneously. Similar results were observed in case of NaCl (Example 5) and IAA (example 6) which demonstrates the chemical inducible behaviour of the transcription activation module. The inventors have further utilized the bidirectional expression to develop a plant gene expression vector module. Such vector comprised of bidirectional promoter, expressing a selection marker like kanamycin resistance (nptII) in one direction and an insecticidal δ-endotoxin coding cryIAc gene in the other direction (Example 7). The Example clearly proves the experimental utility of such developed vector in developing agronomically improved transgenic plants.

The results shown by the designed expression module in transgenic tobacco establish functional validity of the features and the approach utilized by inventors for development of this novel 'bidirectional gene expression module'. It clearly demonstrates the potential application of computational biology, that can be utilized in designing artificial bidirectional expression cassettes for regulated, tissue specific, constitutive and inducible transgene expression in plants. These will clearly have great applications in biotechnology.

References Cited
U.S. Patent documents

| 5359192 | October 1994 | McPherson etal | 800/205 |
| 5424200 | June 1995 | McPerson et al | 435/70 |
| 5627046 | May 1997 | Falconc et al | 435/69 |
| 5814618 | September 1998 | Bajard et al | 514/44 |
| 5837849 | November 1998 | Ellis et al., | 536/24 |
| 6004941 | December 1999 | Bujard et al | 514/44 |
| 6388170 | May 2002 | Gan, et al | 800/278 |

OTHER REFERENCES

Wasylyk, B, "Transcription elements and factors of RNA pol B promoters in higher eukaryotes", CRC, Critical Rev. Biochem. (1988) 23: 77-120

Johnson, P. F. and McKnight, S. L. "Eukaryotic transcription regulatory proteins", Ann. Rev. Biochem. (1989) 58: 799-839.

Fassler, J. S. and Gussin, G. N. "Promoter and basal transcription machinery in bacteria and eukaryotes: Concept, definitions and analogies", Method in Enzymology (1996) 273: 3-29.

Smale, S. T. "Core promoters active contributes of combinatorial gene regulation", Genes & Dev. (2001) 15: 2503-2508.

Sawant, S. Singh, P. K. Madnala R. Tuli, R. "Designing of an artificial expression cassette for high-level of expression of transgenes in plants", Theor. Appl. Genet. (2001) 102: 635-644.

Iann R., Frederic N., Veronique G., Manfred T., "Combination of viral promoter sequences to generate highly active promoter for heterologous therapeutic protein over expression in plants", Plant Science (2002) 162: 833-842.

Benefy, P. N. Ren, L. and Chua, N.-H., "Combinatorial and synergestic properties of CaMV 35S enhances sub doamins", EMBO, (1990) 9: 1685-1696.

Benfey, P. N. and Chua, N.-H., "The cauliflower mosaic virus 35S promoter: Combinatorial regulation of transcription in plants". Science (1990) 250: 959-966.

Odell, J. J., Nagy, F. and Chua, N.-H., "Identification of DNA sequences required for activity of the cauliflower mosaic virus 35S promoter", Nature (1985) 313: 810-812.

Xie, M., He, Y. and Gan, S., "Bidirectionalization of polar promoter in plants." Nature Biotechnology (2001) 19: 677-679.

The invention claimed is:

1. A transgenic plant transformed with a plant transformation vector comprising a bidirectional promoter comprising:
   a) a Transcription Activation Module comprising the nucleotide sequence of SEQ ID NO:1, and
   b) a Transcription Initiation Module comprising the nucleotide sequence of SEQ ID NO:2 that is designed to function as a minimal sequence to initiate transcription of a gene placed downstream, wherein the Transcription Initiation Module is on a first side and a second side of the Transcription Activation Module;
   wherein the bidirectional promoter expresses a selection marker and a reporter gene, said selection marker being expressed by transcription in a direction opposite to transcription of said reporter gene.

2. The plant according to claim 1, wherein the selection marker is selected from the group consisting of nptII, bar and hpt.

3. The plant according to claim 1, wherein the reporter gene is selected from the group consisting of gusA, gfp and luc.

* * * * *

SEQUENCE LISTING

<160> NUMBER OF SEQ ID NOS: 2

<210> SEQ ID NO 1
<211> LENGTH: 312
<212> TYPE: DNA
<213> ORGANISM: Artificial Sequence
<220> FEATURE:
<223> OTHER INFORMATION: This sequence was artificially designed

<400> SEQUENCE: 1

```
gtcgaccatc atttgaaagg gcctcggtaa taccattgtg gaaaaagttg gtaatacgga      60
aaaagaagat tcatcatcca gaaaaggtgt ggaaaagttg tggattgcgt ggaaaaagtt     120
cgatctgacc atctctagat cgtggaaaaa gttcacgtta gcgcttacgt acatatgtgg     180
attgtggaaa aagaagacgg aggcatcggt ggaaaaagaa gcttgtacgc tgtacgctga     240
cgatagatag atacacgtgc acgcgtccac ttgacgcaca attgacgcac aatgacgcca     300
cttgacgcta ct                                                         312
```

<210> SEQ ID NO 2
<211> LENGTH: 130
<212> TYPE: DNA
<213> ORGANISM: Artificial Sequence
<220> FEATURE:
<223> OTHER INFORMATION: This sequence was artificially designed -continued

```
<400> SEQUENCE: 2
tcactatata taggaagttc atttcatttg gaatggacac gtgttgtcat ttctcaacaa      60
ttaccaacaa caacaaacaa caaacaacat tatacaatta ctatttacaa ttacatctag     120
ataaacaatg                                                            130
```